(12) United States Patent
Akiyama et al.

(10) Patent No.: US 6,451,971 B1
(45) Date of Patent: Sep. 17, 2002

(54) PHYSIOLOGICALLY ACTIVE PEPTIDES

(75) Inventors: Katsuhiko Akiyama, Tsukuba (JP); Takeshi Goto, Tsukuba (JP); Fumio Fukai, Tokorozawa (JP); Masaaki Ueki, Ota-ku (JP)

(73) Assignee: Hisamitsu Pharmaceutical Co., Ltd., Tosu (JP)

( * ) Notice: Subject to any disclaimer, the term of this patent is extended or adjusted under 35 U.S.C. 154(b) by 0 days.

(21) Appl. No.: 09/526,879

(22) Filed: Mar. 16, 2000

(30) Foreign Application Priority Data

Mar. 16, 1999 (JP) .......................... 11-070127

(51) Int. Cl.$^7$ .................. A61K 38/00; A61K 38/04; A61K 39/00; A61K 39/04; C07K 16/00; C07K 17/00; C07K 5/00; C07K 7/00; C07K 14/00; C07K 2/00; C07K 4/00

(52) U.S. Cl. ............. 530/326; 530/300; 530/324; 424/184.1

(58) Field of Search ................... 530/324, 300, 530/326; 424/184.1

(56) References Cited

FOREIGN PATENT DOCUMENTS

WO       WO 84/00540     *  2/1984

OTHER PUBLICATIONS

Komazawa et al. 1993, Biol. Pharm. Bull. 16(10)997–1003.*
Dermer, Bio/Technology, vol. 12, p. 320, Mar. 1994.*
Jain et al., Cancer and Metatasis Review, vol. 9, pp. 253–266.*
Benet et al., pp. 3–32, in The Pharmacological Basis of Therapeutics, 8th ed., 1990.*
Int.J.Cancer:43,449–457 (1989) Use of the Membrane Invasion Culture System (MICS) as a Screen for Anti–Invasive Agents, Danny R. Welch et al.
Brief description of Japanese document No. (2).
Review article Adhesion Receptors of the Immune System, Timothy A. Springer, vol. 346, Aug. 2, 1990, pp. 425–434.
Review Article Fibronectins—Adhesive Glycoproteins of Cell Surface and Blood, Nature vol. 275, Sep. 21, 1978. K.M. Yamada et al, pp. 179–184.
Cell. vol. 56, 281–290, Jan. 27, 1989 Changes in Integrin Receptors on Oncogenically Transformed Cells, I.c. Plantefaber et al.
Laminin and Fibronectin Promote the Haptotatic Migration of B16 Mouse Melanoma Cells in Vitro, J.B. McCarthy et al, pp. 1474–1480 The Journal of Cell Biology, vol. 98, Apr. 1984.
Cell attachment activity of fibronectin can be duplicated by small synthetic fragments of the molecule, M.D. Pierschbacher et al. Nature vol. 309, May 3, 1984, pp. 30–33.
Cell, vol. 40, 191–198, Jan. 1985, Identification and Isolation of a 140 kd Cell surface Glycoprotein with Properties Expected of a fibronectin Receptor, Pytela, et al.
A Synthetic Peptide from Fibronectin Inhibits Experimental Metastasiis of Murine Melanoma cells, M.J. Humphries et al, Science, ol 233, Jul. 1986, pp. 467–470.
Jpn. J. Cancer Res. 84, 558–565, May 1993, Antimetastatic Activity of Polymeric RGDT Peptides conjugated with Poly (ethylene glycol) Ikuo Saiki et al.
Biochemical and Biophysical Research Communications 220, 394–398, (1996) Fibronectin Harbors Anticell Adhesive Activity, Fumio Fukai et al.
Brief description of Japanese document No. (13).
Biol. Pharm. Bull. 16 (10) 997–1003 (1993) Synthetic Arg–Gly–Asp–Ser Analogues of the Cell Recognition Site of Fibronectin That Retain Antimetastatic and Anti–cell Adhesive Properties Hiroyuki Komazawa et al.
Primary Sructure of Fibronectin, Torben E. Petersen et al. Department of Molecular Biology and Plant Physiology; University of Aarhus, DK–8000 Arhus C, Denmark, pp. 1–7.
The Journal of Biological Chemistry, vol. 270, No. 37, Issue of Sep. 15, pp. 21612–21618, 1996 Requirement for the Synergy Site for Cell Adhesion to Fibronectin Depends on the Activation State of Integrin $_\alpha 5_\beta 1$*, Erik H.J. Danen et al.
The Journal of Biological Chemistry, vol. 270, No. 44 of Nov. 3, pp. 26270–26277, 1995. Regulation of Integrin $_\alpha 5_\beta 1$–Fibronectin Interactions by divalent Cations. A.Paul Mould et al.
The Journal of Biological Chemistry, vol. 266, No. 14, Issue of May 15, 1991, pp 8807–8813. Rat Plasma Fibronectin Contains two Distinct Chemotactic Domains for Fibroblastic Cells * Fumio Fukai et al.
Journal of Virology, Sep. 1997, p. 6541–6546, Equine Infectious Anemia Virus Utilizes a YXXL Motif within the Late Assembly Domain of the Gag p9 Protein. Bridget A. Puffer et al.
Journal of Biological Chemistry vol. 270, No. 49, Issue of Dec. 8, pp. 29111–29116, 1995. Identification of an Active Site Arginine in Rat choline Acetyltransferase by Alanine Scanning Mutagenesis * Donghai wu et al.

(List continued on next page.)

Primary Examiner—Anthony C. Caputa
Assistant Examiner—Natalie Davis
(74) Attorney, Agent, or Firm—Fitch, Even, Tabin & Flannery (57) ABSTRACT

Physiologically active peptides possessing cell adhesion inhibitory activity are provided.

A physiologically active peptide of this invention is characterized by possessing cell adhesion inhibitory activity and comprising 30 amino acid residues or less, as well as by having an amino acid sequence of the formula:

Gly Leu Lys Pro Gly Val Asp X1 Thr Ile Thr X2 X3 Ala X4 wherein
X1 represents Tyr or Ala;
X2 represents Val or Ala;
X3 represents Tyr or Ala; and
X4 represents Val or Ala.

8 Claims, 5 Drawing Sheets

OTHER PUBLICATIONS

Fukai Fumio et al., "Identification of the Anti–Adhesive Site Buried Within the Heparin–Binding Domain of Fibronectin", XP–000915473, Journal of Biochemistry, vol. 121, No. 2, 1997, pp. 189–192.

Ohgi Chizuru et al., "Application of Fibronectin–Derived Anti–Adhesive Peptide to Tumor Metastasis Suppression", XP–000864713, Cell Structure and Function, vol. 22, No. 6, Dec. 1997, pp. 761.

Mohri Hiroshi, "Interaction of Fibronectin with Integrin Receptors: Evidence by Use of Synthetic Peptides", XP–000864714, Peptides (Tarrytown), vol. 18, No. 6, 1997, pp. 899–907.

Hirata Satoshi et al., "Inhibition of Experimental Metastasis of B16–Bl6 Melanoma by Fibronectin–Derived Anti–Adhesive Fragment", XP–000864707, Cell Structure and Function, vol. 21, No. 6, 1996, pp. 681.

Yamada K M et al., "Peptide Inhibitors of Fibronectin Laminin and Other Adhesion Molecules Unique and Shared Features", XP–000864706, Journal of Cellular Physiology, vol. 130, No. 1, 1987, pp. 21–28.

* cited by examiner

PHYSIOLOGICALLY ACTIVE PEPTIDES

BACKGROUND OF THE INVENTION

1. Field of the Invention

This invention relates to novel physiologically active peptides possessing cell adhesion inhibitory activity. These novel physiologically active peptides are useful as therapeutic agents for various diseases which are believed to involve cell adhesion factors and/or ligand molecules to the cell adhesion factors, such as cancer, inflammation including rheumatism, and fibrosis.

2. Related Background Art

Numerous remedies have been tried in the treatment of cancer, and notable therapeutic effects have come to be seen in a number of cancers. Under the present circumstances, methods of treatment for the prevention of cancer metastasis, however, have not yet been established.

When the patient has been diagnosed as having a cancer, principal treatments include a surgical treatment, radiotherapy and chemotherapy. In a case where the patient complains of obvious abnormality, it is almost certain that the patient has the condition of a progressive cancer; therefore, the treatment is not easy. It is no exaggeration that what brings such condition may be, in short, through metastatic growth of the cancer. The prognosis of the patient is almost governed by the degree of cancer metastatis (Welch, et al., Intern. J. Cancer, 43, 449, 1989). Unless the metastatic growth of a cancer can be suppressed, it will be extremely difficult to control the cancer once it has developed. In a situation where a stomach cancer has progressed, it is likely that the cancer has already migrated to the lymph nodes, liver, lung and other organs. The same is true with a breast cancer, and the fact of the matter is that the progressive cancer has migrated not only to its peripheral lymph nodes, but also to the bone marrow or the lung. Particularly, it is the degree of lymphogenous metastasis that determines the prognosis of epithelial cancers (Shigeru Tsukagoshi, Chemistry for the Conquest of Cancer. Pharmacia Review, No. 6: The Pharmaceutical Society of Japan).

Metastasis of a cancer consists of complex steps: beginning with detachment of cancer cells from the primary tumor mass and their invasion into peripheral tissues, and leading to their proliferation in the migrated tissues. Elements, both in the cancer cells and the host, influence these steps. In the former cells, the primary tumor mass comprises a group of cells of ununiformity which exhibit cellular characters differing with respect to proliferation capability, drug susceptibility, immunogenicity, and morphology as a result of incessant gene alternation: the steps involve the elements such as the propensities of cells to migrate and to invade the peripheral tissues, and production of autonomous proliferation factors. The elements on the host side are thought to be physical and anatomic conditions in blood, defense mechanisms by immunocompetent cells, adhesive interactions between vascular endothelial cells and platelets, effects of growth factors from the peripheral tissues of metastases, and the like.

It is believed that during a series of steps forming cancer metastases, the expression and regulation of metastatic characters of cancer cells is determined under the influence of various biological components containing normal cells, cancer cells themselves and extracellular matrices in the host.

Adhesion between cancer cells or between cancer cells and normal cells is mediated by cell adhesion molecules that are expressed on the surfaces of cells. The cadherin family (Masatoshi Takechi, Molecular Basis for Tissue Construction-the Role of Cadherin in Cell Recognition, Biochemistry, 59, 1, 1987), the immunoglobulin family and the selectin family (Springer, T. A., Nature, 346, 425, 1990) are known as cell adhesion molecules. Adherent molecules on the surfaces of cells, including the integrin family, are known to be involved in adhesion between cancer cells and extracellular matrices including glycoproteins such as fibronectin, laminin and collagen, and proteoglycans to which heparan sulfate or chondroitin sulfate is bound. These extracellular matrix molecules are deeply involved in the metastasis of cancer.

It has been shown that when cells are transformed to malignancy by oncogenic viruses or carcinogens, the synthesis of extracellular matrix molecules, such as fibronectins, and their extracellular accumulation diminishes (Yamada, K. M. and Olden, K., Nature 275, 179, 1978), and that the level of expression of integrin molecules diminishes, or adhesiveness to fibronectins is reduced (Plantfaber, L. C. and Hynes, R. O., Cell 56, 281, 1989). It has also been reported that both fibronectin and laminin promote the adhesion of cancer cells as well as their motility (McCarthy, J. B., J. Cell Biol., 98, 1474, 1984).

Fibronectin and laminin molecules have domain structures through which many functions are dispersed within their molecules. While the structures have been elucidated by techniques, biochemically or through genetic engineering, the presence of cell adhesion sites and receptors thereto have been discovered. The RGD sequence within the cell-binding domain of fibronectin has been identified to be a cell recognition sequence (Pierschbacher, M. D., Nature 309, 30, 1984); it has been determined that the sequence also exists and functions in many cell adhesion related molecules and that its cell receptor is $\alpha 5\beta 1$ integrin receptor (Pytela, R., Cell 40, 191, 1985).

For the reasons stated above, as adhesive interactions between the cell adhesion molecules and cells have become apparent, attempts are being made to make use of the peptides that antagonize cell adhesion as anti-metastatics of cancer.

Humphries et al. discloses that GRGDS peptide, which functions as a cell adhesion signal of fibronectin, inhibits the experimental metastasis of melanoma cells to the lung (Humphries, M. J., Science 233, 467, 1986).

However, there are many problems to be solved before the peptide can be put to practical use as drug: for example, the rate of clearance of the peptide from the circulation following administration is fast, and it is liable to be decomposed by enzyme (Saiki, I., et al., Jpn. J. Cancer Res., 84, 558, 1993).

Fukai et al. reports that when a 30-kDa fragment derived from the Hep2 domain of fibronectin (referred to as "Hep2" hereafter) is denatured with urea, it acquires a strong cell adhesion inhibitory activity (Fukai, F., et al., Biochemica. Biophys. Res. Commun., 220, 394, 1996).

The reference, however, does not disclose which amino acid sequence results in the cell adhesion inhibitory activity by Hep2. Further, because Hep2 consists of 271 amino acid residues, it is undesirable that Hep2 itself be put to practical use as drug for the following reasons among others: the synthesis and preparation of Hep2 is difficult owing to its large molecular weight, and there is the possibility that it exhibits an unfavorable physiological activity since it contains amino acid sequences unrelated to the cell adhesion inhibitory activity.

As stated above, searches for inhibitory substances for cancer metastasis are indispensable for the control of cancers; however, under the present circumstances no substance has yet been obtained that would serve as a specific remedy and thus has been put to practical use.

SUMMARY OF THE INVENTION

In light of the aforementioned circumstances, this invention has been made, and it aims at providing novel physiologically active peptides possessing cell adhesion inhibitory activity.

Furthermore, it is an object of the invention to provide anti-metastatics comprising the novel physiologically active peptides.

The present inventors have diligently pursued further research with the aim toward solving the aforementioned problems and have successfully discovered novel peptides possessing an antagonistic action against the action of cell adhesion factors that promote diseases such as cancer, inflammation and fibrosis and/or against the action of ligand molecules to the cell adhesion factors: the peptides containing a consensus amino acid sequence of Thr Ile Thr and comprising amino acid sequences set forth in SEQ ID NOs: 2, 3, and 7–9 in the Sequence Listing.

These peptides are shorter in segment than Hep2 and possess a strong cell adhesion inhibitory activity without being subjected to denaturation treatment such as urea treatment.

The physiologically active peptides of this invention are also analogous to specific sequences of the amino acid sequence of human fibronectin protein.

Specifically, the invention preferably relates to a physiologically active peptide possessing cell adhesion inhibitory activity and comprising 30 amino acid residues or less, the peptide having an amino acid sequence of the formula SEQ ID NO: 12, Gly Leu Lys Pro Gly Val Asp X1 Thr Ile Thr X2 X3 Ala X4 wherein
X1 represents Tyr or Ala;
X2 represents Val or Ala;
X3 represents Tyr or Ala; and
X4 represents Val or Ala.

Also, the invention relates to the physiologically active peptide described above (SEQ ID NO: 2) wherein X1 is Tyr, X2 is Val, X3 is Tyr, and X4 is Val.

Also, the invention relates to the physiologically active peptide described above (SEQ ID NO:3) wherein X1 is Ala, X2 is Val, X3 is Tyr, and X4 is Val.

Also, the invention relates to the physiologically active peptide described above (SEQ ID NO: 7) wherein X1 is Tyr, X2 is Ala, X3 is Tyr, and X4 is Val.

Also, the invention relates to the physiologically active peptide described above (SEQ ID NO: 8) wherein X1 is Tyr, X2 is Val, X3 is Ala, and X4 is Val.

Also, the invention relates to the physiologically active peptide described above (SEQ ID NO: 9) wherein X1 is Tyr, X2 is Val, X3 is Tyr, and X4 is Ala.

Further, the invention relates to an anti-metastatic of cancer containing any of the physiologically active peptides described above.

Also, the invention relates to the anti-metastatic of cancer described above wherein the physiologically active peptide is further conjugated with biotin.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

DESCRIPTION OF THE PREFERRED EMBODIMENTS

This invention will be explained in detail by referring to embodiments thereof hereinbelow.
(Physiological Activity)

In this invention, the term "cell adhesion factor" refers to a factor which has an action similar to that of the cadherin-catenin family, the integrin family, the immunoglobulin super family, the CD44 family, the selectin family and the sialomucin family that have been discovered as factors which are involved in adhesion between cells or between cells and extracellular matrices and that are recognized as classes of molecules participating in the intracellular signal transduction system, ontogeny, organomorphosis, wound healing in addition to adhesion. (Yoshiyuki Ishii, Invasion and Metastatis of Cancers, Clinical Application of Basic Research, Igakushoin Co. Ltd., 207–215, 1998.) Further, the term "cell adhesion activity" refers to an antagonistic action against such adhesion between cells and/or between cells and extracellular matrices.

The physiologically active peptides of this invention have sequences totally different from those of the peptides containing the RGD sequence that have hitherto been reported (Humphries, M. J., et al., Science, 233,467, 1986; Komazawa, H., et al., Biol. Pharm. Bull., 16, 10,0997, 1993). It is thus thought that their cell adhesion inhibitory activity is not due to the action mediated by receptors on which the RGD peptides have been reported to act.

Japanese Unexamined Patent Application Hei 10-147600 describes that peptides containing at least Tyr-Thr-Ile-Tyr-Val-Ile-Ala-Leu, which is an amino acid sequence derived from Hep2, are provided with an anti-cell adhesion action and the peptides are useful as anti-metastatics of cancer. However, these peptides are different from the peptides of this invention possessing cell adhesion inhibitory activity in amino acid sequence as well as in action.

Surprisingly, these differences in amino acid sequence will lead to distinctions in cell adhesion inhibitory activity against certain cell lines.

Specifically, the peptides described in Japanese Unexamined Patent Application Hei 10-147600 exhibit cell adhesion inhibitory activity against, for example, A375SM cell line derived from human melanoma, as well as against K562 cell line derived from human chronic myelocytic leukemia, U937 cell line derived from human hystiocytic lymphoma and Ramos cell line derived from human Burkitt's lymphoma: although latter cell lines (anchorage-independent cells) would not naturally exhibit adhesiveness against extracellular matrices, they acquire adhesiveness by having been subjected to special treatment.

By contrast, the peptides of this invention possess cell adhesion inhibitory activity against the K562 cell line derived from human chronic myelocytic leukemia, the U937 cell line derived from human hystiocytic lymphoma and the Ramos cell line derived from human Burkitt's lymphoma, but they neither exhibit the cell adhesion inhibitory activity against the A375SM cell line derived from human melanoma nor against HT1080 cell line derived from human fibrosarcoma.

(Physiologically Active Peptides)

A physiologically active peptide of this invention is characterized by having an amino acid sequence with a preferable number of amino acids and exhibiting the cell adhesion inhibitory activity. The physiologically active peptide of the invention is also analogous to the sequence at a specific site of the amino acid sequence of the human fibronectin protein.

Furthermore, the anti-metastatic of cancer according to this invention contains as ingredient, at least one of the physiologically active peptides of the invention, and is based on its cell adhesion inhibitory activity.

More specifically, for the first consensus amino acid sequence, the physiologically active peptide of this invention has the sequence (Thr Ile Thr) which is also Nos. 1575–1577 of the amino acid sequence of the human fibronectin protein. Further, the second consensus amino acid sequence is that which is obtained by attaching Ala, which is also No. 1580 of the amino acid sequence of the human fibronectin protein, to the C-terminus of the amino aid sequence Thr Ile Thr via two amino acid residues ($X_2$, $X_3$) and by further attaching one amino acid ($X_4$) thereto. Such two amino acids are not particularly limited, but they are preferably Ala, Val or Tyr. Also, the one amino acid is not particularly limited, but it is preferably Ala or Val.

A further consensus amino acid sequence is that which is obtained by attaching Gly Leu Lys Pro Gly Val Asp, which is also Nos. 1567–1573 of the amino acid sequence of the human fibronectin protein, to the N-terminus of the amino aid sequence Thr Ile Thr via one amino acid residue ($X_1$). Such one amino acid is not particularly limited, but it is preferably Ala or Tyr.

There are no particular limitations to the total number of amino acids for a physiologically active peptide of this invention as explained above. However, it is preferably 30 residues or less, more preferably 20 residues or less, from the standpoints of the ease and efficiency of synthesis, the stability of storage, the handling, and the like. The locations of the aforementioned consensus amino acid sequences are also non-limiting.

Furthermore, the physiologically active peptides of this invention include peptides that are obtained by making amino acid additions, deletions, or substitutions to the three kinds of consensus amino acid sequence by one or more amino acids, insofar as their cell adhesion activity is not impaired.

As particularly shown in SEQ ID NOs: 3, 7, 8 and 9, an amino acid is substituted that corresponds to one of amino acid nos. 1574, 1578, 1579 and 1581, which are shown in the literature on fibronectin: Petersen T. E. et al., Fibronectin, Academic Press, New York, 1–24, 1988. This allows one to obtain an effect equal to or greater than the cell adhesion inhibitory activity of the peptide set forth in SEQ ID NO: 2.

There are also no particular limitations to the kind of amino acid to be substituted; however, one can obtain cell adhesion inhibitory activity equal to or greater than that of the peptide set forth in SEQ ID NO: 2 by substituting amino acids at the aforementioned positions with alanine. Especially, the peptide set forth in SEQ ID NO: 3 possesses much greater cell adhesion inhibitory activity compared to the peptide set forth in SEQ ID NO: 2.

The physiologically active peptides of this invention encompass the structures that are obtained by repeatedly bonding the three consensus amino acid sequences plural times and that possess the cell adhesion inhibitory activity.

The physiologically active peptides of this invention also encompass those that are obtained by attaching (or conjugating) to the aforementioned amino acid sequences, various modifying groups or substituents to impart other functions. For example, in order to enhance hydrophilicity, it is possible to attach (or conjugate) to the physiologically active peptide, a hydrophilic amino acid or a substance bearing a hydrophilic group such as ethylene glycol, PEG, polysaccharide or a decomposition product thereof.

The physiologically active peptides of this invention also encompass their various derivatives possessing the cell adhesion inhibitory activity based thereon. For example, mentioned are modification with polymers such as polyethylene glycol (PEG) and cyclization of the straight chain peptides (Saiki, I., et al., Jpn. J. Cancer Res., 84, 558, 1993).

In like manner, it is also possible to modify a peptide of this invention by modifying the side chain of an amino acid constituting the peptide, e.g., by the use of ester or ether linkages provided that the cell adhesion inhibitory activity is not impaired.

The amino acid sequences of physiologically active peptides of this invention are believed to possess the specific action because of higher structures that the sequences have. Therefore, similar effects can be expected if compounds that mimic the dimensional structures of the peptides are synthesized.

There are no particular limitations to obtaining the physiologically active peptides of this invention. Methods of chemical synthesis, biological methods, and methods of gene manipulation all of which are intended for ordinary oligopeptides can preferably be used. For the method of chemical synthesis, solid phase synthesis is preferably usable, for example. Methods of peptide purification that are ordinarily known in the art, e.g., column chromatography, can preferably be used to purify the peptides thus obtained. Further, preparation by chemical synthesis is most commonly done by using a commercially available peptide synthesizer. There are also no particular limitations to obtaining the peptides of this invention by gene manipulation, and protein expression systems that are known in the art may be used. For example, a DNA sequence encoding the peptide of the invention is inserted into a plasmid vector and a microorganism such as E. coli is transformed to produce the peptide; the method of synthesis using such a technique of gene manipulation or the like allows the synthesis. More specifically, a gene encoding the physiologically active peptide is synthesized, for example, with a DNA synthesizer; the gene is incorporated into a known plasmid vector; the resulting recombinant vector is introduced into a microorganism that will serve as a host; and a transformant is prepared. This will allow the physiologically active peptide to be produced. Any expression vector for peptide production can be used without particular limitation for the plasmid vector that is used here. In addition, the host is not limited to a microorganism, and a eucaryotic cell such as COS cell may be used.

(Application)

The physiologically active peptides of this invention are useful as anti-metastatics of cancer that inhibit metastatis of cancers based on the cell adhesion inhibitory activity possessed by the peptides.

The physiologically active peptides of the invention are also useful as testing reagents for investigating various diseases in which adhesion between cells or between cells and extracellular matrices is implicated. They are also useful as therapeutic agents against these diseases. For example, they are useful for cancer, rheumatism, asthma, allergic conditions, thrombosis, organ transplant rejections, wound healing such as fibrosis, inflammation, immunoinflammatory conditions including enteritis such as ulcerative colitis, and autoimmune diseases.

In administering the physiologically active peptides of this invention as the therapeutic agents, methods of oral or parental administration in addition to methods of directly administering them to target organs or tissues may be used. The oral administration includes sublingual administration. The parental administration includes injections (such as subcutaneous injection, intramuscular injection, intraveous injection, arterial injection and intravenous drip), suppositories, ointments and patches.

Dosages depend on the age of the subject, the route of administration or the number of administration, and may be varied accordingly. In these cases, an effective amount to be administered as a composition of an effective amount of the physiologically active peptide of this invention with a suitable diluent or a physiologically acceptable carrier is from 1 to 100,000 μg/kg weight/day; and it will be administered daily once to a few times in divided doses, or will be administered once every few days. The physiologically active peptides of this invention encompass those conjugated with other peptides, e.g., biotin.

When the physiologically active peptide of this invention are orally administered, tablets, granules, fine granules, powders, capsules, and the like that are adapted for the administration normally contain binders, inclusion agents excipients, disintegrators, etc. in their compositions and they can take any form of peroral liquid preparations, suspensions, emulsions, syrups, and the like. When parental administration is employed, it may include stabilizers, buffers, preservatives, isotonizing agents, and the like; and forms of a unit dosage ample, a multi-dosage container and a tube may be provided.

Further, this invention embraces a screening method for discovering an antagonist against a physiologically active peptide of the invention by which the cell adhesion inhibitory action possessed by the physiologically active peptide is used as an index of judgement. Furthermore, the invention embraces the antagonist obtained by such a screening method. The antagonists provide new insight on the cell adhesion inhibitory action and enable the development of novel therapeutic agents for cancer or the like.

Moreover, this invention embraces antibodies raised against the physiologically active peptides of the invention as antigens. Use of the antibodies will allow the construction of labeling agents that can monitor the point of cell adhesion inhibitory action.

The physiologically active peptide of this invention is characterized by possessing cell adhesion inhibitory activity and comprising 30 amino acid residues or less, as well as by having an amino acid sequence of the formula:

Gly Leu Lys Pro Gly Val Asp X1 Thr Ile Thr X2 X3 Ala Val wherein

X1 represents Tyr or Ala;

X2 represents Val or Ala; and

X3 represents Tyr or Ala.

Also, the anti-metastatic of the invention is based on such physiological activity.

This invention will be concretely explained by way of examples hereinbelow; however, these examples are not intended to be limiting upon the scope thereof.

EXAMPLES

Example 1

Synthesis of Peptides and their Modification with Biotin

All peptides used in the test were synthesized using a peptide synthesizer (Multiple Peptide Synthesizer, MultiSynTec; GmbH). The sequences of the synthesized peptides were determined with a peptide sequencer (Model 476A; Applied Biosystems).

To increase the solubility of the synthesized peptides, the peptides were subjected to biotin conjugation for further use according to the following method. After 1 mg of peptide was dissolved in 750 μl of dimethyl sulfoxide (DMSO), 50 μl of 200 mM carbonate buffer (pH 8.5) was added. To this was further added 2 μl of DMSO solution containing Biotin (long arm)-NHS (Vector Laboratories, Inc.) (50 mg/ml). Stirring was carried out at 4° C. overnight to effect biotin conjugation of peptide.

The activating group of the unreacted Biotin (long arm)-NHS was blocked by adding ethanolamine (to give a final concentration of 50 mM) and stirring at room temperature for 1 h. The reaction mixture after conjugation was loaded onto a Sephadex G-15 column, and the biotin conjugate of peptide was purified by gel filtration separation. The peptides were quantified with a BCA Protein Assay Kit (Pierce Inc.).

Example 2

Evaluation of Cell Adhesion Inhibitory Activity of Synthetic Peptide on Anchorage-Independent Cells It was reported that manganese ion ($Mn^{2+}$) activates integrins by acting on cells that originally do not exhibit adhesiveness against an extracellular matrix. (Danen et al., J. Biol. Chem., 270, 37, 21612, 1995; Mould et al., J. Biol. Chem., 270, 44, 26270, 1995.) This allows the cells to acquire adhesiveness to the extracellular matrices mediated by integrins. Such experimental induction of adhesion can be utilized as models for cell adhesion in the processes of metastatis of cancer cells and infiltration of inflammatory cells into tissues.

The K562 cell line derived from human chronic myelocytic leukemia, U937 cell line derived from human hystiocytic lymphoma and Ramos cell line derived from human Burkitt's lymphoma (all available from American Type Tissue Culture Collection-ATCC), which are one kind of anchorage-independent cells, were then treated with $Mn^{2+}$ to prepare a system, where the cell adhesion inhibitory activity of the peptides was evaluated.

Ninety six well plates were coated with fibronectin, which is one kind of extracellular matrix: fibronectin (FN) was prepared by the method of Fukai et al., J. Biol. Chem., 266, 8807, 1991. After cells were suspended to a cell density of $2\times10^5$/ml in a HEPES buffered physiological saline containing 0.1 mM $Mn^{2+}$, the cells (100 µl) were added to the plate and incubated at 37° C. under 5% $CO_2$ for 60 min. Concurrently with addition of the cell suspension, the biotinylated peptide as synthesized in Example 1 (the amino acid sequence of the peptide portion is set forth in SEQ ID NO: 2) was added to the plate to give a final concentration of from 50 to 200 µg/ml. As a control group, a known peptide possessing cell adhesion inhibitory activity (SEQ ID NO: 10; Japanese Unexamined Patent Application Hei 10-147600) was added to the plates in like manner. As a negative control, the group to which only biotin (unbound with the peptide) had been added was also evaluated.

FN coating was carried out by adding to each well, FN phosphate buffer (100 µl) that had been prepared to 10 µg/ml, by conducting incubation at 37° C. under 5% $CO_2$ for 60 min and then by washing the well with phosphate buffer 3 times. After cells in each well were fixed with 5% formaldehyde (Wako Pure Chemical Industries, Ltd.), unbound cells were removed and five areas were randomly selected in each well to count the cells under a microscope.

Figure 1:
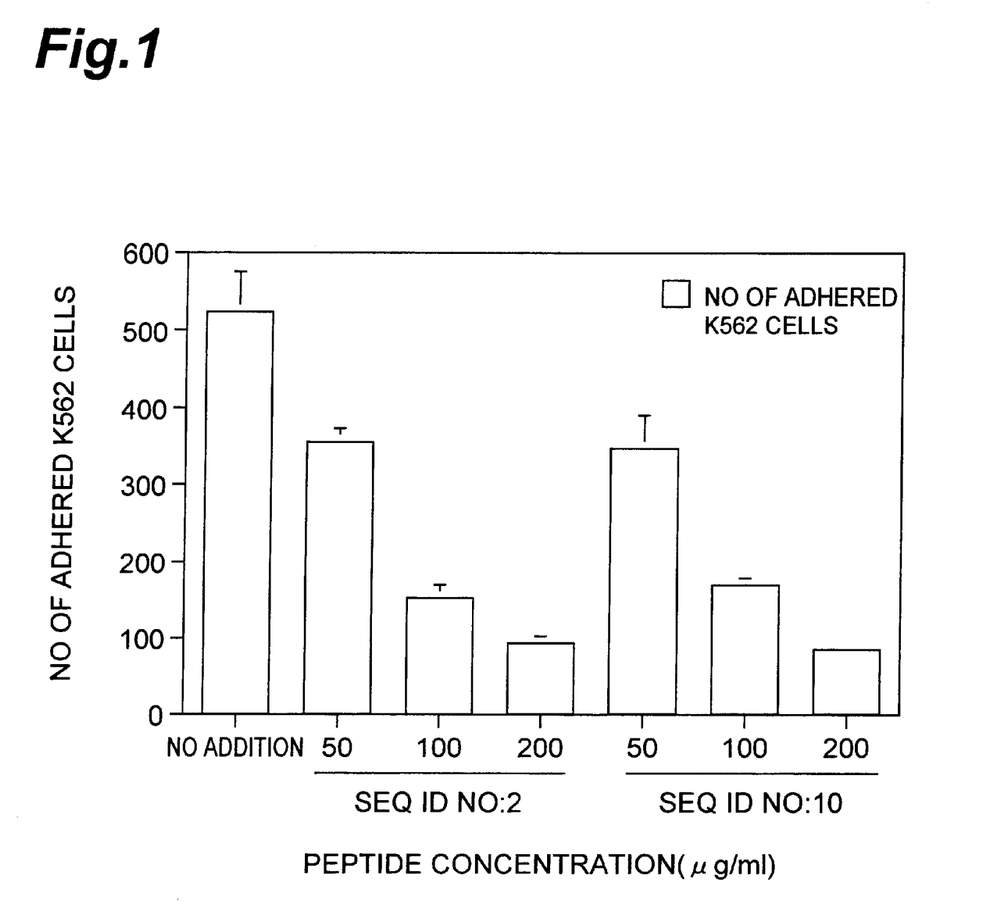
FIG. 1 is a graph showing that the cell adhesion inhibitory effect of the peptide set forth in SEQ ID NO: 2 is nearly equal to the activity of a known cell adhesion inhibitory peptide (SEQ ID NO: 10).
Figure 2:
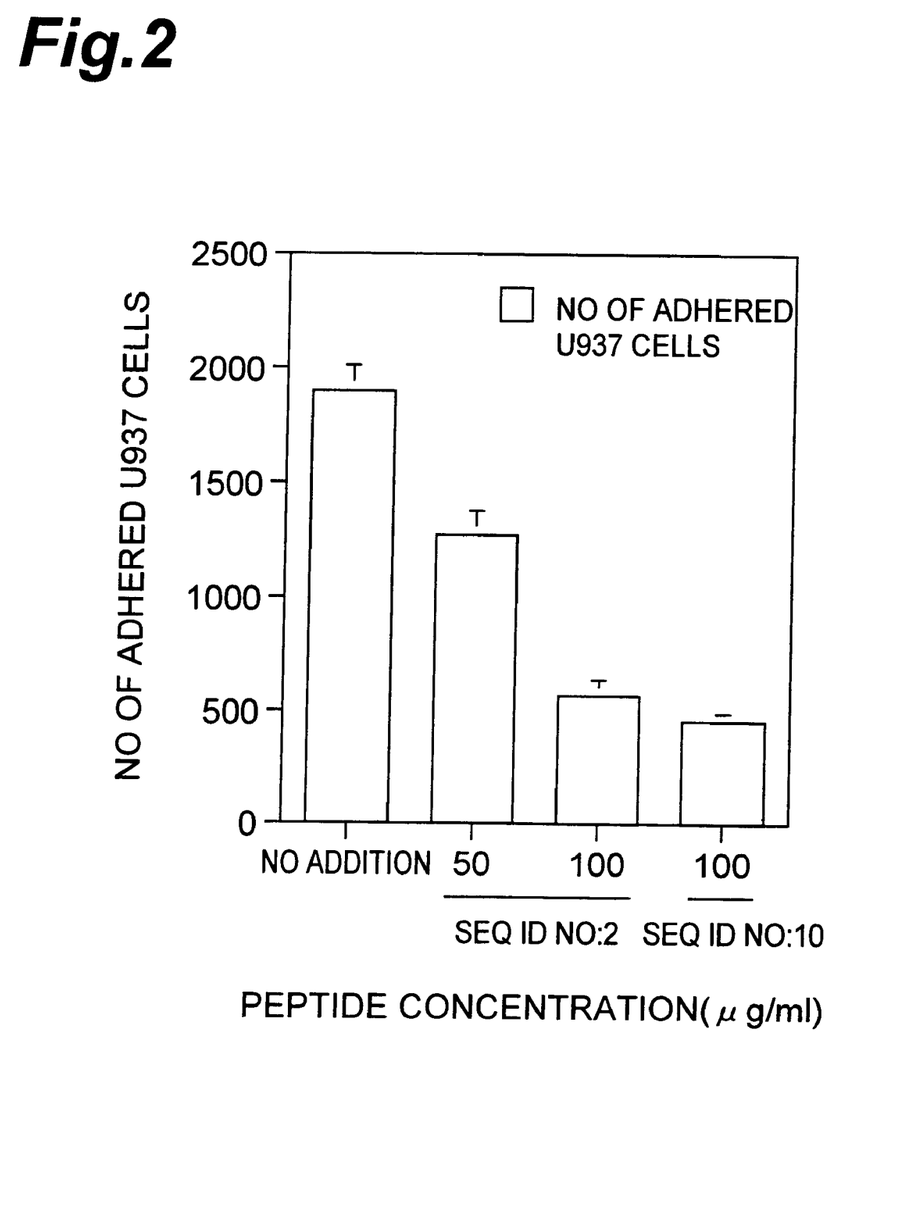
FIG. 2 is a graph showing that the cell adhesion inhibitory effect of the peptide set forth in SEQ ID NO: 2 is nearly equal to the activity of the known cell adhesion inhibitory peptide (SEQ ID NO: 10).
Figure 3:
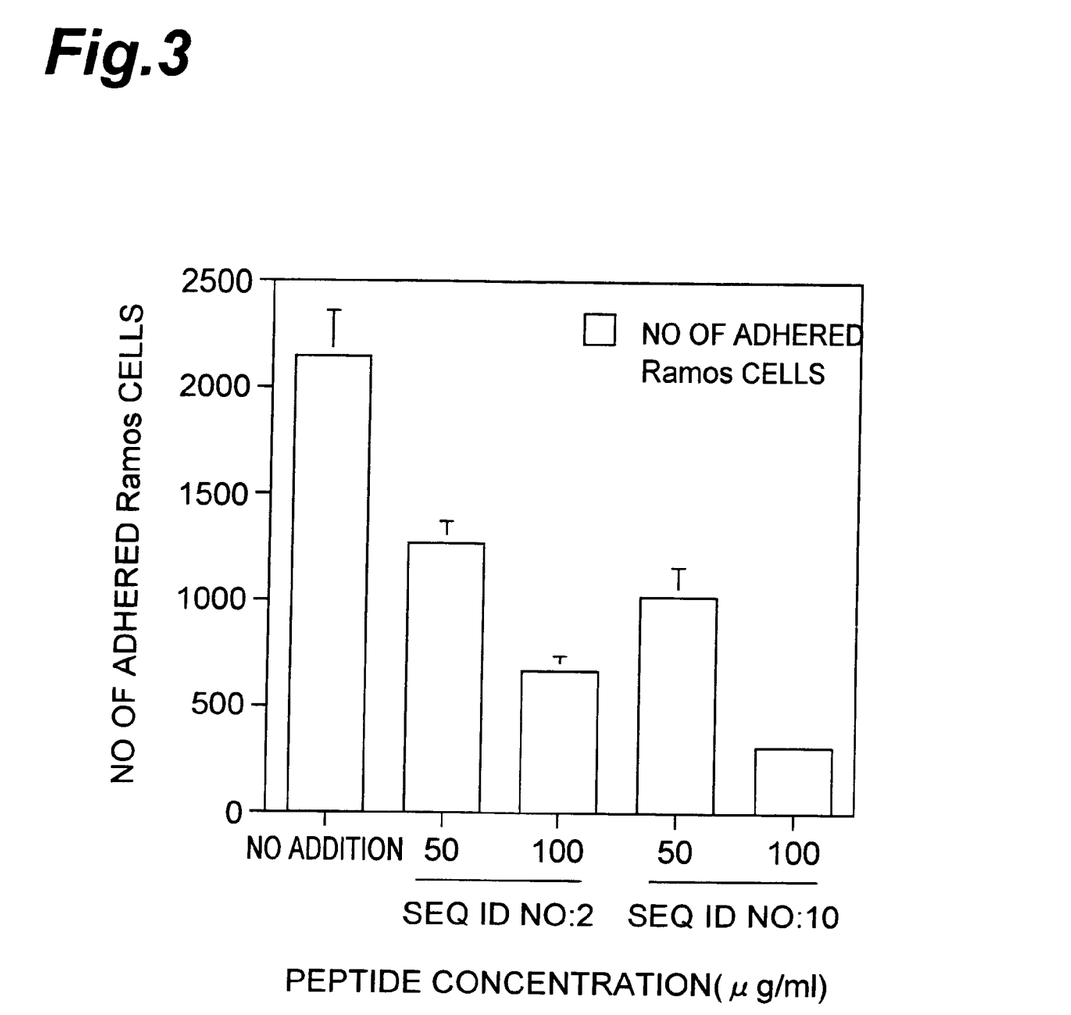
FIG. 3 is a graph showing that the cell adhesion inhibitory effect of the peptide set forth in SEQ ID NO: 2 is nearly equal to the activity of the known cell adhesion inhibitory peptide (SEQ ID NO: 10).

As FIGS. 1, 2, and 3 show, it is apparent that the cell adhesion inhibitory effect of the peptide set forth in SEQ ID NO: 2 is nearly equal to the activity of the known cell adhesion inhibitory peptide (SEQ ID NO: 10).

Example 3

Evaluation of Cell Adhesion Inhibitory Activity of Synthetic Peptide on Anchorage-Dependent Cells The human melanoma A375SM cells and human fibrosarcoma HT1080 (both available from ATCC), which are anchorage-dependent cells, were used in the evaluation. Cell adhesion inhibitory activity was evaluated according to the method of Fukai et al. as described in Biochem. Biophys. Res. Commun., 220, 394–398, 1996. The number of spread cells was counted as an index of the cell adhesion inhibitory activity.

A375SM cells or HT1080 cells were prepared to $2\times10^5$/ml in Dulbecco's Modified Eagle Medium (DMEM: GIBCO BRL) containing 0.1% Ovalbumin (Wako Pure Chemical Industries, Ltd.). This cell suspension (100 µl) was added to 96-well plates that had been coated with fibronectin or vitronectin (VN), which are one kind of extracellular matrix, and incubated at 37° C. under 5% $CO_2$ for 60 min. Concurrently with addition of the cell suspension, the biotinylated peptide as synthesized in Example 1 was added to the plates to give a final concentration of from 50 to 200 µg/ml. As a control group, the known peptide possessing cell adhesion inhibitory activity (SEQ ID NO: 10; Japanese Unexamined Patent Application Hei 10-147600) was added to the plate in like manner. FN and VN coatings were carried out by adding to each well, FN or VN phosphate buffered saline (100 µl) that had been prepared to 0.5 µg/ml, by conducting incubation at 37° C. under 5% $CO_2$ for 60 min and then by washing the well with phosphate buffered saline 3 times. After cells in each well were fixed with 5% formaldehyde (Wako Pure Chemical Industries, Ltd.), unbound cells were removed and five areas were randomly selected in each well to count the spreading cells under a microscope.

Figure 4:
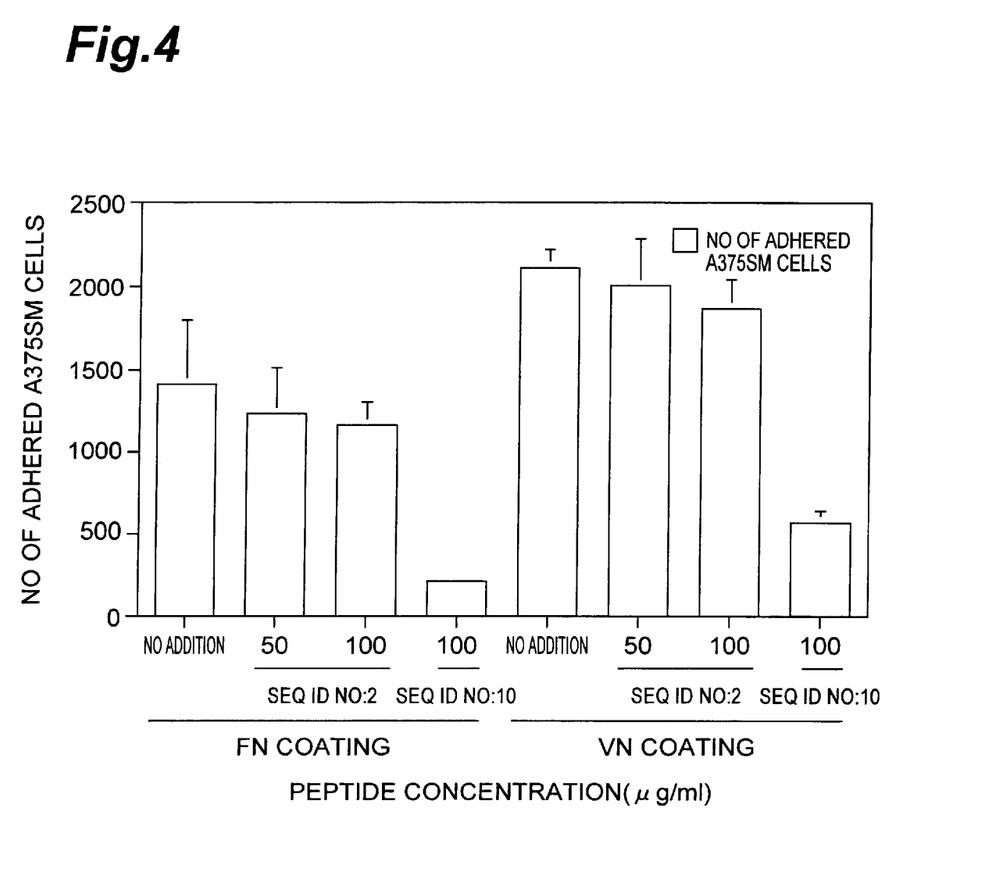
FIG. 4 is a graph showing that the known cell adhesion inhibitory peptide (SEQ ID NO: 10) possesses a cell spreading inhibitory action whereas the peptide set forth in SEQ ID NO: 2 exhibits no such action at all.
Figure 5:
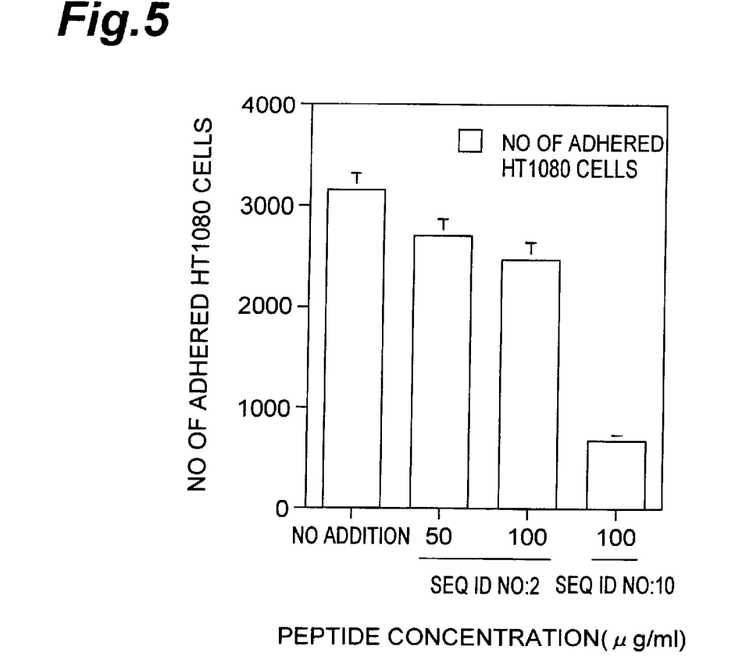
FIG. 5 is a graph showing that the known cell adhesion inhibitory peptide (SEQ ID NO: 10) possesses a cell spreading inhibitory action whereas the peptide set forth in SEQ ID NO: 2 exhibits no such action at all.

As FIGS. 4 and 5 show, the known cell adhesion inhibitory peptide (SEQ ID NO: 10) had a cell adhesion inhibitory action whereas the peptide set forth in SEQ ID NO: 2 exhibited no such action at all.

Example 4

Identification of Amino Acid Sequence Regions Essential to Cell Adhesion Inhibitory Activity by Alanine Scanning Method The alanine scanning method is a technique that is used to identify amino acid sequence regions essential to physiological activities of proteins and peptides. (Puffer et al., J. Virol., 71, 6541, 1997; Wu and Hersh, J. Biol. Chem., 270, 49, 29111, 1995.) This method was then employed to analyze the present peptides. The peptides listed in Table 1, all of which were biotinylated (Example 1), were used in the experiments. For evaluation, the K562 cells derived from human chronic myelocytic leukemia, which was one kind of anchorage-independent cell, were used.

TABLE 1

```
SEQ ID NO: 2
Gly Leu Lys Pro Gly Val Asp Tyr Thr Ile Thr Val Tyr Ala Val
SEQ ID NO: 3
Gly Leu Lys Pro Gly Val Asp Ala Thr Ile Thr Val Tyr Ala Val
SEQ ID NO: 4
Gly Leu Lys Pro Gly Val Asp Tyr Ala Ile Thr Val Tyr Ala Val
SEQ ID NO: 5
Gly Leu Lys Pro Gly Val Asp Tyr Thr Ala Thr Val Tyr Ala Val
SEQ ID NO: 6
Gly Leu Lys Pro Gly Val Asp Tyr Thr Ile Ala Val Tyr Ala Val
SEQ ID NO: 7
Gly Leu Lys Pro Gly Val Asp Tyr Thr Ile Thr Ala Tyr Ala Val
SEQ ID NO: 8
Gly Leu Lys Pro Gly Val Asp Tyr Thr Ile Thr Val Ala Ala Val
SEQ ID NO: 9
Gly Leu Lys Pro Gly Val Asp Tyr Thr Ile Thr Val Tyr Ala Ala
```

Evaluation of the cell adhesion inhibitory activity was conducted similarly to Example 2. Results were shown in FIG. 6.

Figure 6:
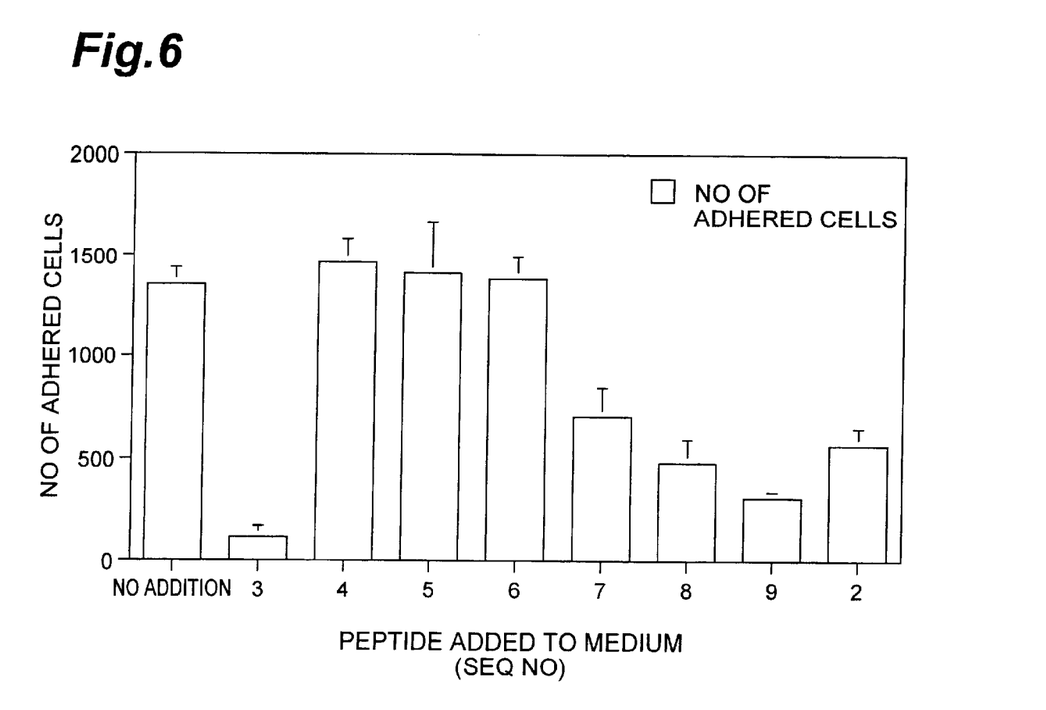
FIG. 6 is a graph showing the results of evaluation of the cell adhesion inhibitory activities.

When the peptide set forth in SEQ ID NO: 2, which was a sequence derived from human serum fibronectin, was added for testing, the cell adhesion inhibitory activity was noted. By contrast, the cell adhesion inhibitory activity was lost in SEQ ID NOs: 4, 5 and 6 among the peptides (SEQ ID NOs: 3–9) wherein one amino acid contained in SEQ ID NO: 2 was substituted by alanine. Further, SEQ NO: 3 possessed a stronger cell adhesion inhibitory activity than did SEQ NO: 2.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A peptide possessing cell adhesion inhibitory activity and consisting of 15 amino acids, said peptide having an amino acid sequence of the formula:

Gly Leu Lys Pro Gly Val Asp X1 Thr Ile Thr X2 X3 Ala X4 wherein

X1 represents Tyr or Ala;

X2 represents Val or Ala;

X3 represents Tyr or Ala; and

X4 represents Val or Ala, as set forth in SEQ ID NO:12 of the Sequence Listing.

2. The peptide according to claim 1, wherein X1 is Tyr, X2 is Val, X3 is Tyr, and X4 is Val, as set forth in SEQ ID NO: 2 in the Sequence Listing.

3. The peptide according to claim 1, wherein X1 is Ala, X2 is Val, X3 is Tyr, and X4 is Val, as set forth in SEQ ID NO: 3 in the Sequence Listing.

4. The physiologically active peptide according to claim 1, wherein X1 is Tyr, X2 is Ala, X3 is Tyr, and X4 is Val, as set forth in SEQ ID NO. 7 in the Sequence Listing.

5. The physiologically active peptide according to claim 1, wherein X1 is Tyr, X2 is Val, X3 is Ala, and X4 is Val, as set forth in SEQ ID NO: 8 in the Sequence Listing.

6. The physiologically active peptide according to claim 1, wherein X1 is Tyr, X2 is Val, X3 is Tyr, and X4 is Ala, as set forth in SEQ ID NO: 9 in the Sequence Listing.

7. An anti-metastatic of cancer containing the peptide according to any claims 1–6.

8. The anti-metastatic of cancer according to claim 7, wherein the peptide is conjugated with biotin.

* * * * *

```
                              SEQUENCE LISTING

<160> NUMBER OF SEQ ID NOS: 13

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence:
      Physiologically active peptide

<400> SEQUENCE: 1

Thr Ile Thr Val Tyr Ala Val
 1               5

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence:
      Physiologically active peptide

<400> SEQUENCE: 2

Gly Leu Lys Pro Gly Val Asp Tyr Thr Ile Thr Val Tyr Ala Val
 1               5                  10                  15

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence:
      Physiologically active peptide

<400> SEQUENCE: 3

Gly Leu Lys Pro Gly Val Asp Ala Thr Ile Thr Val Tyr Ala Val
 1               5                  10                  15

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence:
      Physiologically active peptide

<400> SEQUENCE: 4

Gly Leu Lys Pro Gly Val Asp Tyr Ala Ile Thr Val Tyr Ala Val
 1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence:
      Physiologically active peptide

<400> SEQUENCE: 5

Gly Leu Lys Pro Gly Val Asp Tyr Thr Ala Thr Val Tyr Ala Val
 1               5                  10                  15
```

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence:
      Physiologically active peptide

<400> SEQUENCE: 6

Gly Leu Lys Pro Gly Val Asp Tyr Thr Ile Ala Val Tyr Ala Val
 1               5                  10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence:
      Physiologically active peptide

<400> SEQUENCE: 7

Gly Leu Lys Pro Gly Val Asp Tyr Thr Ile Thr Ala Tyr Ala Val
 1               5                  10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence:
      Physiologically active peptide

<400> SEQUENCE: 8

Gly Leu Lys Pro Gly Val Asp Tyr Thr Ile Thr Val Ala Ala Val
 1               5                  10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence:
      Physiologically active peptide

<400> SEQUENCE: 9

Gly Leu Lys Pro Gly Val Asp Tyr Thr Ile Thr Val Tyr Ala Ala
 1               5                  10                  15

<210> SEQ ID NO 10
<211> LENGTH: 21
<212> TYPE: PRT
<213> ORGANISM: Artificial Sequence
<220> FEATURE:
<223> OTHER INFORMATION: Description of Artificial Sequence:
      Physiologically active peptide

<400> SEQUENCE: 10

Thr Glu Ala Thr Ile Tyr Gly Leu Glu Pro Gly Thr Glu Tyr Thr Ile
 1               5                  10                  15
Tyr Val Ile Ala Leu
             20

<210> SEQ ID NO 11
<211> LENGTH: 8
<212> TYPE: PRT
<213> ORGANISM: Artificial Sequence

```
<220> FEATURE:
<223> OTHER INFORMATION: Description of Artificial Sequence:
      Physiologically active peptide

<400> SEQUENCE: 11

Tyr Thr Ile Tyr Val Ile Ala Leu
 1               5

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence:
      Physiologically active peptide
<221> NAME/KEY: MOD_RES
<222> LOCATION: (8)
<223> OTHER INFORMATION: Tyr or Ala
<221> NAME/KEY: MOD_RES
<222> LOCATION: (12)
<223> OTHER INFORMATION: Val or Ala
<221> NAME/KEY: MOD_RES
<222> LOCATION: (13)
<223> OTHER INFORMATION: Tyr or Ala
<221> NAME/KEY: MOD_RES
<222> LOCATION: (15)
<223> OTHER INFORMATION: Val or Ala

<400> SEQUENCE: 12

Gly Leu Lys Pro Gly Val Asp Xaa Thr Ile Thr Xaa Xaa Ala Xaa
 1               5                  10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence:
      Physiologically active peptide
<221> NAME/KEY: MOD_RES
<222> LOCATION: (8)
<223> OTHER INFORMATION: Tyr or Ala
<221> NAME/KEY: MOD_RES
<222> LOCATION: (12)
<223> OTHER INFORMATION: Val or Ala
<221> NAME/KEY: MOD_RES
<222> LOCATION: (13)
<223> OTHER INFORMATION: Tyr or Ala

<400> SEQUENCE: 13

Gly Leu Lys Pro Gly Val Asp Xaa Thr Ile Thr Xaa Xaa Ala Val
 1               5                  10                  15
```